(12) United States Patent
Medghalchi et al.

(10) Patent No.: US 8,247,188 B2
(45) Date of Patent: Aug. 21, 2012

(54) FAS BINDING ANTIBODIES

(75) Inventors: Susan Medghalchi, Ellicott City, MD (US); Jennifer L. Aldrich, Frederick, MD (US)

(73) Assignee: Fasgen Diagnostics, LLC, Baltimore, MD (US)

( * ) Notice: Subject to any disclaimer, the term of this patent is extended or adjusted under 35 U.S.C. 154(b) by 696 days.

(21) Appl. No.: 11/465,403

(22) Filed: Aug. 17, 2006

(65) Prior Publication Data
US 2007/0148718 A1    Jun. 28, 2007

Related U.S. Application Data

(60) Provisional application No. 60/709,246, filed on Aug. 17, 2005.

(51) Int. Cl.
*C07K 16/40* (2006.01)
*C07K 16/30* (2006.01)
*C12N 5/20* (2006.01)
*G01N 33/543* (2006.01)
*G01N 33/573* (2006.01)
*G01N 33/574* (2006.01)
*G01N 33/577* (2006.01)
*A61K 39/395* (2006.01)

(52) U.S. Cl. .......... 435/7.4; 422/412; 422/420; 435/7.9; 435/7.93; 435/7.94; 435/7.95; 435/70.21; 435/40.5; 435/40.52; 435/338; 435/287.2; 435/287.7; 435/975; 436/512; 436/514; 436/518; 436/64; 436/813; 530/388.26; 530/388.8; 530/391.3

(58) Field of Classification Search .................. 435/7.4, 435/7.9, 7.94, 7.95, 70.21, 338, 40.5, 40.52, 435/287.2, 975, 7.93, 287.7; 436/518, 64, 436/813, 512, 514; 530/388.26, 388.8, 391.3; 422/412, 420
See application file for complete search history.

(56) References Cited

U.S. PATENT DOCUMENTS 5,864,011 A    1/1999   Kuhajda et al.
5,872,217 A *  2/1999   Kuhajda et al. ............. 530/387.7

OTHER PUBLICATIONS

Kuhajda et al., 1994. Fatty acid synthesis: a potential selective target for antineoplastic therapy. Proc. Natl. Acad. Sci. USA 91: 6379-6383.*
Jayakumar et al., 1995. Human fatty acid synthase: properties and molecular cloning. Proc. Natl. Acad. Sci. USA 92: 8695-8699.*
Hellström et al., 1985. In Monoclonal Antibodies for Cancer Detection and Therapy (Baldwin et al, eds.), Academic Press, London. p. 20.*
Harlow et al., 1988. Antibodies. A Laboratory Manual, Cold Spring Harbor Laboratory, Cold Spring Harbor. pp. 72-77.*
Oh et al., 1992. Quantitative differentiation of the haptoglobin-related gene product from haptoglobin in human plasma: a possible test for tumor-associated antigen. Hybridoma 11: 1-12.*
Wang et al., 2001. Two-site ELISA for the quantitative determination of fatty acid synthase. Clinica Chimica Acta 304: 107-115.*
Wright, Michael, E., et al. "Androgen Receptor Represses the Neuroendocrine Transdifferentiation Process in Prostate Cancer Cells", *Molecular Endocrinology* (2003) 17(9):1726-1737.
Anonymous (BD Transduction Laboratories), "Fatty Acid Synthase"[Online] Feb. 10, 2004, XP002409529, retrieved on Nov. 28,2006 from the Internet: URL:http://www.ebiotrade.com /buyf/productsf/BD%20Pharmingen/610962.pdf>.
Pizer, Ellen S., et al. "Increased Fatty Acid Synthase as a Therapeutic Target in Adrogen-Independent Prostate Cancer Progression", *The Prostate* (2001) 47:102-110.
Anonymous (FASGEN): "FAS-detect™ IHC"—Specification Sheet—Product No. A-1001, [Online] Nov. 2, 2005, XP-002409531, retrieved on Nov. 23, 2006 from the Internet: URL:http://www.fasgen.com/fas-diag/FASdetectIHC_insert_051102_rev3.pdf>.
Shah, Uzma S., et al. "Fatty acid synthase gene overexpression and copy number gain in prostate adenocarcinoma", *Human Pathology* (2006) 37:401-409.
Linden, Daniel, et al. "Liver-directed overexpression of mitochondrial glycerol-3-phosphate acyltransferase results in hepatic steatosis, increased triacylglycerol secretion and reduced fatty acid oxidation", *The FASEB Journal* (2006) 20(3):434-443.

* cited by examiner

*Primary Examiner* — Gail R Gabel
*Assistant Examiner* — James L Grun
(74) *Attorney, Agent, or Firm* — Patentique PLLC

(57) ABSTRACT

The disclosed invention relates to monoclonal antibodies (MAbs) which recognize human fatty acid synthase (hFAS) and are distinct from previously known anti-hFAS antibodies. Compositions, devices and kits comprising the MAbs are provided along with methods of using the MAbs in a variety of applications.

12 Claims, 8 Drawing Sheets

FAS BINDING ANTIBODIES

RELATED APPLICATIONS

This application claims benefit of priority from U.S. Provisional Patent Application 60/709,246, filed Aug. 17, 2005, which is hereby incorporated by reference as if fully set forth.

FIELD OF THE DISCLOSED INVENTION

The disclosed invention relates to monoclonal antibodies (MAbs) which recognize human fatty acid synthase (hFAS). Compositions, devices and kits comprising the MAbs are provided along with methods of using the MAbs in a variety of applications.

BACKGROUND OF THE DISCLOSED INVENTION

A prognostic molecule found in tumor cells from breast cancer patients was identified as fatty acid synthase (FAS). See Kuhajda et al. (1994) "Fatty acid synthesis: a potential selective target for antineoplastic therapy." *Proc Natl Acad Sci USA.*, 91(14):6379-83. FAS is an approximately 270-kDa polypeptide, and tumor fatty acid synthase oxidizes NADPH in a malonyl-CoA-dependent fashion and synthesized fatty acids composed of 80% palmitate, 10% myristate, and 10% stearate from acetyl-CoA, malonyl-CoA, and NADPH with a specific activity of 624 nmol of NADPH oxidized per min per mg. Studies with tumor cell lines with elevated fatty acid synthase expression demonstrated that fatty acid synthase increases occur in the context of overall cellular increases in endogenous fatty acid synthesis. FAS was also identified as the target for inhibition by cerulenin-mediated inhibition of acylglycerol synthesis in cells.

Subsequently, FAS was recognized as playing the key role in enzyme mediated, de novo fatty acid synthesis. FAS expression has been shown to be involved in carcinogenesis of human malignancies beyond breast to include colorectal and prostate carcinomas. See for example, Shurbaji et al. (1996) "Immunohistochemical detection of a fatty acid synthase (OA-519) as a predictor of progression of prostate cancer." *Hum Pathol.* 27(9):917-21, where an affinity purified FAS antibody was used to examine primary prostate cancers by immunohistochemistry.

Two archetypal monoclonal antibodies (MAbs) which bind FAS have been identified and used in an enzyme linked immunosorbent assay (ELISA) to quantify FAS. See Wang et al., "A new model ELISA, based on two monoclonal antibodies, for quantification of fatty acid synthase." (2002) *J Immunoassay Immunochem.* 23(3):279-92. A MAb identified as M6 was used as the capture antibody in the ELISA while a MAb identified as M3 was labeled and used as a detector antibody. The ELISA based on this two MAb combination was recognized as an improvement over previous assays based on an earlier polyclonal-monoclonal combination ELISA described by Wang et al. ("Two-site ELISA for the quantitative determination of fatty acid synthase." *Clin Chim Acta.* 304(1-2):107-15, (2002)).

Innocenzi et al. ("Fatty acid synthase expression in melanoma." *J Cutan Pathol.* 30(1):23-8, (2003)) also describe experiments with use of the M6 antibody. Krontiras et al. ("Fatty acid synthase expression is increased in neoplastic lesions of the oral tongue." *Head Neck* 21(4):325-9, (1999)) describe the use of antibodies from ChekTec of Baltimore, Md., which offered M3 and M6 as anti-OA-519 antibodies. Pizer et al. ("Increased fatty acid synthase as a therapeutic target in androgen-independent prostate cancer progression." *Prostate* 47(2):102-10 (2001)) used antibodies as described in U.S. Pat. No. 5,864,011, which is related to U.S. Pat. No. 5,759,791, as discussed below.

The above discussion and citation of documents herein is not intended as an admission that any is pertinent prior art. All statements as to the date or representation as to the contents of documents is based on the information available to the applicant and does not constitute any admission as to the correctness of the dates or contents of the documents.

SUMMARY OF THE DISCLOSED INVENTION

The disclosed invention provides antibodies which recognize epitopes of human fatty acid synthase (hFAS) and thus bind to hFAS polypeptides, including fragments thereof. Embodiments of the disclosed invention include antibodies which bind full length as well as particular hFAS polypeptides to varying degrees not previously known. Other embodiments include antibodies which bind to one or more hFAS polypeptides to the exclusion of other hFAS polypeptides. The disclosed invention also provides for compositions and preparations, devices and apparatuses, articles of manufacture, and methods comprising the antibodies described herein. Further embodiments of the disclosed invention include modified or derivative forms of the disclosed antibodies, including hybrid antibodies, altered antibodies, chimeric antibodies, conjugated antibodies, single chain antibodies, and humanized antibodies as non-limiting examples. Other modified forms include portions of the disclosed antibodies, including Fab, Fab', F(ab')$_2$ and Fv fragments which bind hFAS polypeptides.

Thus in a first aspect, the disclosed invention provides antibodies that bind hFAS polypeptides, including fragments thereof, and are different from previously known FAS binding antibodies. In some embodiments, the antibodies are monoclonal antibodies, which are a composition or preparation of antibodies with a homogeneous antibody population without regard for the source of the antibody population or the means by which the antibody population was made or prepared. In other embodiments, the antibodies are a mixture of monoclonal antibodies such that the population of antibodies is heterogeneous in the mixture.

The monoclonal antibodies of the disclosed invention are distinct in binding characteristics, and thus binding specificity, from previously known hFAS binding antibodies, such as the M3 and M6 monoclonal antibodies, as well as the anti-Hpr monoclonal antibody referred to in U.S. Pat. No. 5,759,791 as produced by hybridoma cells OA-519-M1 or HPR-2 and deposited under ATCC accession number 10853. While anti-Hpr antibodies have been observed to crossreact with FAS, the disclosed invention is directed to anti-hFAS antibodies which, in some embodiments, do not crossreact with Hpr.

Without being bound by theory, and offered to improve the understanding of the disclosed invention, it is believed that the antibodies of the disclosed invention differ in structure from previously known hFAS binding antibodies within at least one of the CDRs (complementarity determining regions) which participate in binding to an hFAS polypeptide. This belief is based in part on the well documented structural arrangement of elements, including the CDR containing $V_L$ and $V_H$ hypervariable regions, of an antibody's structure. Of course antibodies of the disclosed invention may also differ from known hFAS binding antibodies at more than one CDR and/or at more than one amino acid position within one or more CDR. These differences may provide the antibodies of the disclosed invention with the characteristic of binding to a different epitope than previously known antibodies against FAS.

Accordingly, the disclosed invention also provides a CDR from an hFAS binding antibody that is distinct from the CDR of previous FAS binding antibodies, such as the M3 or M6 antibodies. A CDR of the disclosed invention may be in an isolated form from the antibody in which it is normally found. Isolation may be by proteolytic cleavage from the antibody or by sequencing and isolation of the nucleic acid sequence encoding a CDR (or CDR portion) of an antibody. The CDR, or a polypeptide containing the CDR, can be recombinantly linked to another polypeptide to form a fusion protein, or used to replace the CDR of another antibody to form a chimeric antibody (or fragment thereof), as non-limiting examples. Such forms and uses of a CDR may be practiced by methods known to the skilled person, including recombinant DNA technology which incorporates the nucleic acid sequence encoding a CDR into a larger sequence encoding a fusion protein or chimeric antibody.

The different binding specificities provided by the antibodies of the disclosed invention provide benefits and advantages for their use. In some embodiments, antibodies that have relatively high specificity for only hFAS polypeptides, in comparison to relatively low cross-reactivity with non-hFAS polypeptides, may be advantageously used in methods where an hFAS polypeptide to be bound by an antibody is in an environment of high complexity. Non-limiting examples of such environments include i) the situation of Western blotting (or immunoblotting) of samples containing numerous other non-hFAS antigens that are exposed to an antibody and ii) immunohistochemistry (IHC) where a sample presents numerous other non-hFAS antigens that are presented to an antibody. In other embodiments, antibodies that have relatively high specificity for full length hFAS polypeptides may be advantageously used to detect full length molecules without comparatively low cross reactivity to shorter hFAS fragments. Alternatively, antibodies that recognize shorter hFAS fragments, and optionally also full length or other fragments, may also be advantageously used to detect proteolytic fragments of hFAS that may be present in some samples, including biological samples from some subjects, but not others.

In further embodiments, antibodies may have specificities for denatured or fixed forms of an hFAS polypeptide. A non-limiting example is the situation of antibodies with specificities for full length, or proteolytic fragments of, hFAS that have been denatured with detergent, such as in the context of Western blotting after SDS gel electrophoresis. Another non-limiting example is in the case of antibodies with specificities for full length, or proteolytic fragments of hFAS that have been fixed with an agent such as, but not limited to formalin, formaldehyde, paraformaldehyde, glutaraldehyde, and/or an alcohol, like in the context of a fixed sample of cells or tissues used in IHC, including a formalin fixed and paraffin embedded (FFPE) sample.

In a second aspect, compositions and preparations comprising the antibodies of the disclosed invention are provided. The compositions or preparations may be those of a relatively crude form, such as those containing an antibody of the disclosed invention and the cell(s) or cellular components used to produce the antibody, as well as those containing complexes of the antibodies bound to one or more hFAS polypeptides. In other embodiments, the compositions or preparations may be those for use in a kit or method as described herein. In further embodiments, the compositions or preparations may be those for application, or coating, of an antibody of the disclosed invention to a device, such as a solution of antibody used to immobilize the antibody on a solid phase.

Of course an immobilized form of an antibody of the disclosed invention is also an aspect provided herein. Non-limiting examples include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In a further aspect, the disclosed invention provides methods comprising the use of an antibody, or a combination of antibodies, of the disclosed invention. As alluded to above, methods for the use of an antibody in a Western blotting or IHC method is contemplated as part of the disclosed invention. Additional methods include those known in the field as enzyme linked immunosorbent assays (ELISAs) and radio-immune assays (RIAs). More generally, however, methods for the detection of an hFAS polypeptide in any context are contemplated. Such methods all have a common feature or mechanism based on either i) detection of an hFAS polypeptide per se by use of an antibody of the disclosed invention or ii) detection of a complex of an antibody of the disclosed invention and an hFAS polypeptide. Both types of detection address the ultimate question of whether an hFAS polypeptide is present. Moreover, and because an antibody of the disclosed invention is used in the detection, the methods may all be viewed as being an immunoassay for hFAS.

The act of detection may be performed, directly or indirectly (as well as qualitatively or quantitatively), as an indicator of the presence, or level, of an hFAS polypeptide. Alternatively, the act may be used to determine the absence of an hFAS polypeptide. The formation of a complex in a method of the disclosed invention may be allowed to occur under immunologically reactive conditions wherein an antibody of the disclosed invention would bind an hFAS polypeptide. Alternatively, a method of the disclosed invention may simply be directed to the detection of the complex after it has formed, under whatever conditions were present for the antibody and hFAS polypeptide. A non-limiting example is a method wherein complex formation occurs in vivo within an organism or cell.

In some embodiments, the detection is for the presence or absence of hFAS in a biological sample, like a fluid or cell containing sample from a subject or individual. The sample may be suspected of containing one or more hFAS polypeptides, in which case the methods of the disclosed invention are used to provide an initial indicator of their presence, or alternatively the sample may have been previously determined to contain one or more hFAS polypeptides, by use of a method of the disclosed invention or another method, in which case the methods of the disclosed invention provide a basis to confirm or contradict the previous determination.

The disclosed invention also provides for the detection of a complex containing an hFAS polypeptide as a means to diagnose the presence of a disease, such as cancer. The detection may also be used in methods to monitor the course, or recurrence, of a disease in a subject based upon the correlation of the presence, or level, of hFAS to the disease. In some embodiments, the disease is cancer of the breast, prostate, colon, ovary, lung, skin (melanoma), oral mucosa or squamous tissue, genito-urinary, gastrointestinal, or any other malignancies such as sarcomas, or lymphoma/leukemia which may express FAS.

The detection of hFAS polypeptide(s) may also be used as part of the clinical or medical care of a patient. In some embodiments, the detection is used in methods to determine whether to administer a FAS inhibitor to a patient based on the presence or level of hFAS polypeptide(s) in a sample from the patient. In additional embodiments, the determination may be directed toward the treatment of disease (including, but not limited to, those described above), which is diagnosed based on the presence or level of hFAS polypeptide(s) in the sample, such that administration of a FAS inhibitor or other agent to treat the disease is palliative. Non-limiting examples of chemotherapy targeted at FAS include those described in U.S. Pat. No. 5,759,837 and US 2002/0173447 A1.

In other embodiments, the determination may be directed toward the prevention of disease, which is indicated as possible based on the presence or level of hFAS polypeptide(s) in the sample, such that administration of a FAS inhibitor or other agent is to prevent the disease from occurring or reducing its severity or extent if it occurs. This aspect of the disclosed invention thus relates to the field of chemoprevention of disease based upon inhibition of fatty acid synthesis as mediated by FAS in disease onset or progression.

Other clinical methods include those wherein a FAS binding antibody is utilized, in whole or in part, as a therapeutic agent. Such methods include the administration of such an antibody, or a FAS binding portion thereof, which binds FAS. In some embodiments, the antibody, or portion thereof, inhibits or reduces FAS activity to a subject in need of such inhibition. In other embodiments, the antibody or portion thereof, is linked or conjugated to another agent to form a conjugate which inhibits or reduces FAS activity. In further embodiments, the other agent is a toxic agent against the cell expressing the FAS activity. The antibody, or portion thereof, may be administered directly as a therapeutic agent, administered as part of a composition of the disclosed invention, administered as part of a conjugate or fusion polypeptide, or administered as a nucleic acid construct which expresses the antibody (or fragment or fusion polypeptide) in a cell or subject.

Further clinical methods include those involved in the providing of medical care to a patient based on the detection of a hFAS polypeptide as described herein. In some embodiments, the methods are related to the providing of diagnostic services based on determining the presence or level of a hFAS polypeptide, with or without inclusion of a medical interpretation of the significance or insignificance of a detected polypeptide. In other embodiments, the method of providing a diagnostic service of the disclosed invention is preceded by a determination of a need for the service. In further embodiments, the method includes acts in the monitoring of the performance of the service as well as acts in the request or receipt of reimbursement for the performance of the service.

Additional embodiments and features are set forth in part in the description that follows, and in part will become apparent to those skilled in the art upon examination of the specification or may be learned by the practice of the disclosed invention. The features and advantages of the disclosed invention may be realized and attained by means of the instrumentalities, combinations, and methods described in the specification.

Definitions

As used herein, units, prefixes, and symbols are generally denoted in their System International de Unites (SI) accepted form. Numeric ranges are inclusive of the numbers defining the range. The headings provided herein are not limitations of the various aspects or embodiments of the disclosed invention which can be had by reference to the specification as a whole. Accordingly, the terms defined immediately below are more fully defined by reference to the specification in its entirety.

The term "human fatty acid synthase" or "hFAS" or refers to the polypeptide previously identified as a cancer related antigen in U.S. Pat. No. 5,759,791 and the patent applications from which it depends. The antigen is also referred to as OA-519 in the field and is defined by the Nomenclature Committee of the International Union of Biochemistry and Molecular Biology (NC-IUBMB) as fatty acid synthase (E.C. 2.3.1.85), as described at www.chem.qmul.ac.uk/iubmb/enzyme/. The terms are not limited to a particular human fatty acid synthase by amino acid sequence but rather any hFAS or fragment thereof that is recognized by an antibody of the disclosed invention. The terms also refer to hFAS proteins or peptides, including fragments of a full length sequence, which remain intracellular as well as cell-free forms found in extracellular environments and bodily fluids. In some cases, a fragment of a full length hFAS is one which is indicative of (unique to) full length hFAS. The terms "polypeptide", "peptide" and "protein" as used herein refer to a polymer of amino acid residues. These terms also encompass polymers containing conservative amino acid substitutions such that the polymer in its entirety retains its functionality, such as the functionality of being recognized by an anti-hFAS antibody of the disclosed invention.

As used herein, "antibody" refers to an immunoglobulin molecule, and fragments thereof, which are immunologically reactive with a particular antigen. The term "antibodies" refers to a plurality of such molecules and is not limited to homogeneous populations of a single type of antibody. The term "antibody" also includes genetically engineered forms such as chimeric antibodies (e.g., humanized murine antibodies), heteroconjugate antibodies (e.g., bispecific antibodies), and recombinant single chain Fv fragments (scFv), and disulfide stabilized (dsFv) Fv fragments (see, for example U.S. Pat. No. 5,747,654). The term "antibody" also includes antigen binding forms of antibodies (e.g., Fab', F(ab')$_2$, Fab, Fv and rIgG. See also, Pierce Catalog and Handbook, 1994-1995 (Pierce Chemical Co., Rockford, Ill.). The term "anti-hFAS" refers to an antibody which is generated against hFAS.

Humanized antibodies refer to antibodies, or immunologically active fragments thereof, which contain one or two non-human CDRs in a molecule containing human antibody sequences. The non-human CDR(s) may be from any source, including, but not limited to, mouse, rat, rabbit, or other mammalian antibodies. The presence of human portion(s) in a humanized antibody, or fragment thereof, is less likely to cause an immune response when administered to a human subject. A humanized antibody, or fragment thereof, may contain about 50% or more, about 55% or more, about 60% or more, about 65% or more, about 70% or more, about 75% or more, about 80% or more, about 85% or more, about 90% or more, or about 95% or more human antibody sequences over the length of the antibody or fragment thereof.

An antibody immunologically reactive with hFAS as described herein can be generated by known methodologies such as immunization of an antibody producing animal with an hFAS polypeptide. Monoclonal antibodies may be obtained by various techniques familiar to those skilled in the art. Description of techniques for preparing such monoclonal antibodies may be found in, e.g., Stites, et al. (eds.) BASIC AND CLINICAL IMMUNOLOGY (4TH ED.), Lange Medical Publications, Los Altos, Calif., and references cited therein; Harlow & Lane, supra; Goding, MONOCLONAL ANTIBODIES: PRINCIPLES AND PRACTICE (2D ED.), Academic Press, New York, N.Y. (1986); Kohler & Milstein, Nature 256:495497 (1975); and particularly (Chowdhury, P. S., et al. Mol. Immunol. 34:9 (1997)), which discusses one non-limiting method of generating monoclonal antibodies.

Methods to prepare monoclonal antibodies include the immunization of an animal with a nucleic acid sequence that encodes the desired immunogen, in this case, an hFAS polypeptide. This technique has at least two advantages over protein-based immunization: avoidance of the need for protein purification; and increased likelihood of proper post-translational modification of the immunogen.

Generally, an immunoglobulin molecule has two types of polypeptide chains: a heavy and light chain. There are two of each heavy and light chain in the molecule, which gives rise to two binding sites in each molecule. Each chain contains a constant region and a variable region. The variable regions of one light and one heavy chain variable regions contain a "framework" region interrupted by three hypervariable regions, also called complementarity-determining regions or CDRs. See, SEQUENCES OF PROTEINS OF IMMUNOLOGICAL INTEREST, Kabat, E., et al., U.S. Department of Health and Human Services, (1987); which is incorporated herein by reference. Within a species, the sequences of the framework regions of different light or heavy chains are relatively conserved. The combined framework regions of one light and one heavy chain, positions the CDRs in three dimensional space to permit them to interact with and bind to an epitope of an antigen. The CDRs are typically referred to as CDR1, CDR2, and CDR3, numbered sequentially starting from the N-terminus of each chain.

As used herein, the phrase "single chain Fv" or "scFv" refers to an antibody in which a heavy chain and a light chain of a traditional two chain antibody have been joined to form one chain with a single binding site. Typically, a linker peptide is placed between the two chains to allow for proper folding and positioning of the variable region to create the active binding site. The term "linker peptide" refers to a polypeptide chain within an antibody binding fragment (e.g., Fv fragment) which serves to indirectly attach the variable heavy chain to the variable light chain.

More generally, a "linker" is a molecule used to join the antibody to another molecule. The linker is capable of forming covalent bonds to both the antibody and to the other molecule. Suitable linkers are well known to the skilled person and include, but are not limited to, straight or branched chain carbon linkers, hetero cyclic carbon linkers, or peptide linkers. Where the antibody and another molecule are polypeptides, the linkers may be joined to the constituent amino acids through their side groups (e.g., through a disulfide linkage to cysteine). Alternatively, the linkers will be joined to the alpha carbon amino and carboxyl groups of the terminal amino acids.

The term "contacting" refers to placement in direct physical association, such as the placement of an antibody of the disclosed invention with a hFAS polypeptide such that formation of a complex of these two components may result.

The phrase "determining the presence or absence" of an hFAS polypeptide or a complex comprising an hFAS polypeptide as used herein refers to a qualitative assessment of the presence or absence of an hFAS polypeptide in a sample or other material. The term may also be considered the detection of the presence of an hFAS polypeptide above a specific level, such as, but not limited to, a level above background noise or the level in a reference cell or sample (including a cell or sample from a normal subject). The use of "determining" or "detecting" the level of an hFAS polypeptide as used herein refers to the assessment of the amount of a polypeptide at a quantitative or semi-quantitative level. The assessment need not be absolutely accurate but may instead be approximate.

The terms "conjugate", "bond", "link", and variations thereof refer to the physical attachment of two entities via formation of at least one covalent bond. In some situations, they refer to making two polypeptides into one contiguous polypeptide molecule. In the context of the disclosed invention, the terms include reference to joining an antibody moiety to a solid phase support or other solid phase material, including the surface of a solid phase material, as well as another molecule. The formation of a covalent bond may be by use of a chemical reaction to form the bond. The term "support" refers to conventional supports such as beads, particles, dipsticks, fibers, filters, membranes and silane or silicate supports such as glass slides. Conjugated antibodies of the disclosed invention include, but are not limited to, antibodies that are attached to a label as well as antibodies attached to a toxin or other desired moiety, including another polypeptide, such that the antibody may act as a targeting molecule which directs the toxin or other moiety to a desired FAS expressing target. Optionally, the target is a cell, such as a diseased cell.

The term "label" refers to a composition capable of being detected (directly or indirectly) to indicate the presence of the "labeled" molecule. Thus a labeled antibody of the disclosed invention may be detected by virtue of the label. The detection may be made quantitatively or qualitatively. Suitable labels include one member of a binding pair (such as biotin in a biotin-avidin or biotin-strepavidin binding pair), radioisotopes, nucleotide chromophores, enzymes (e.g., horse radish peroxidase, alkaline phosphatase and others commonly used in an ELISA), substrates, fluorescent molecules (e.g., fluorescein isothiocyanate, Texas red, rhodamine, green fluorescent protein, and the like), chemiluminescent moieties, magnetic particles or beads, bioluminescent moieties, calorimetric labels such as colloidal gold, and the like. As such, a label is any composition detectable, directly or indirectly, by spectroscopic, photochemical, biochemical, immunochemical, electrical, optical or chemical means. In some embodiments, the label is detectable by the unaided eye.

The means to detect such labels are well known to the skilled person. For example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The term "FAS inhibitor" includes any number of compounds and molecules currently known or later developed to act as inhibitors of fatty acid synthase activity. Non-limiting examples are provided in U.S. Pat. No. 5,759,837, which is hereby incorporated in its entirety as if fully set forth. Other non-limiting examples include thiolactomycin (see WO 04/005277, PCT/US03/021700, for a non-limiting description) and those described in WO 2004/006835 A2 (PCT/US03/020960). As described below, an antibody, or immunologically active fragment thereof, may also be a FAS inhibitor.

and anti-human monoclonal FAS, M6 clone, in Lane 2; M3 clone in Lane 3 against the 250 kDa FAS. Both 34-6E7 and 347C3 also react strongly with FAS at 250 kDa and an FAS fragment at 134 kDa. Unlabeled lanes contain reactions with other monoclonal antibodies.

Figure 1:
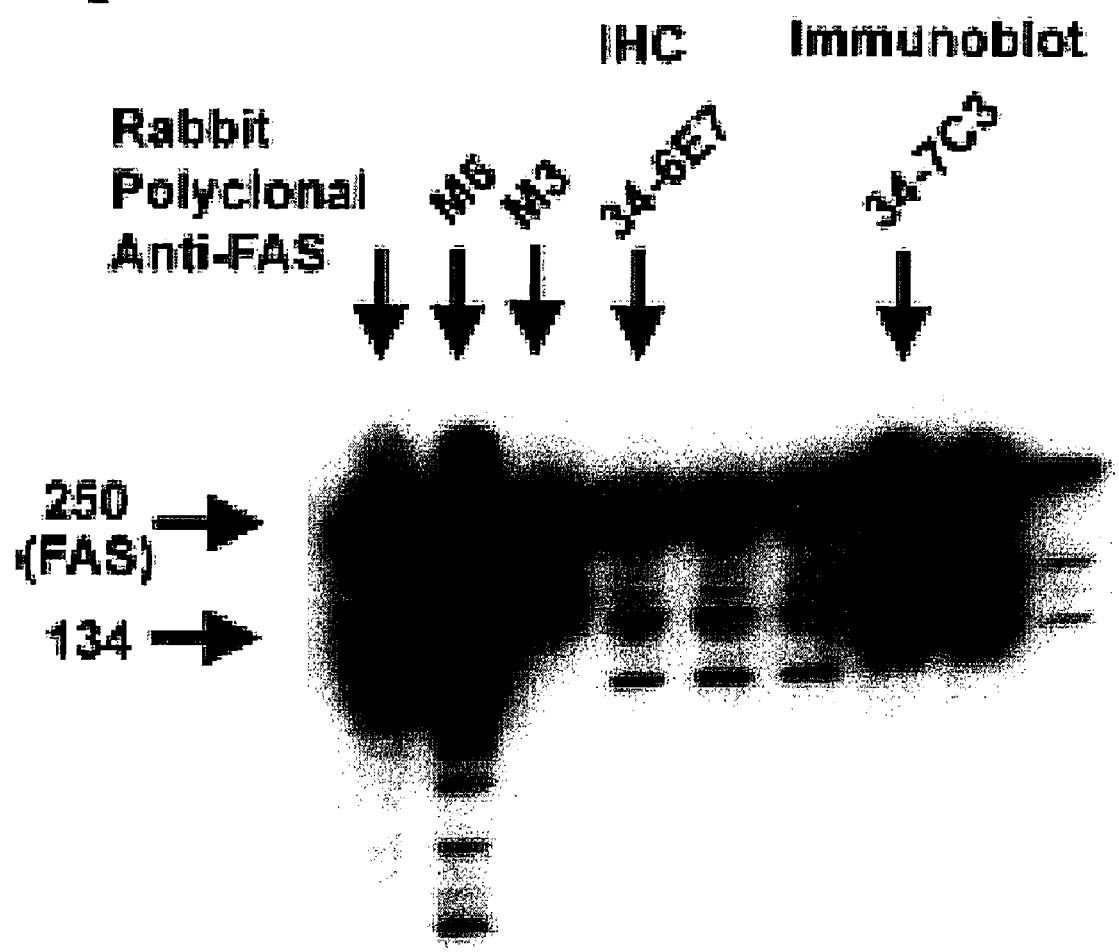
FIG. 1 is an immunoblot of lysate from MCF-7 human breast cancer cells, which overexpress hFAS. Lanes 1-3 demonstrate reactivity of a rabbit polyclonal anti-FAS (Lane 1)
Figure 2:
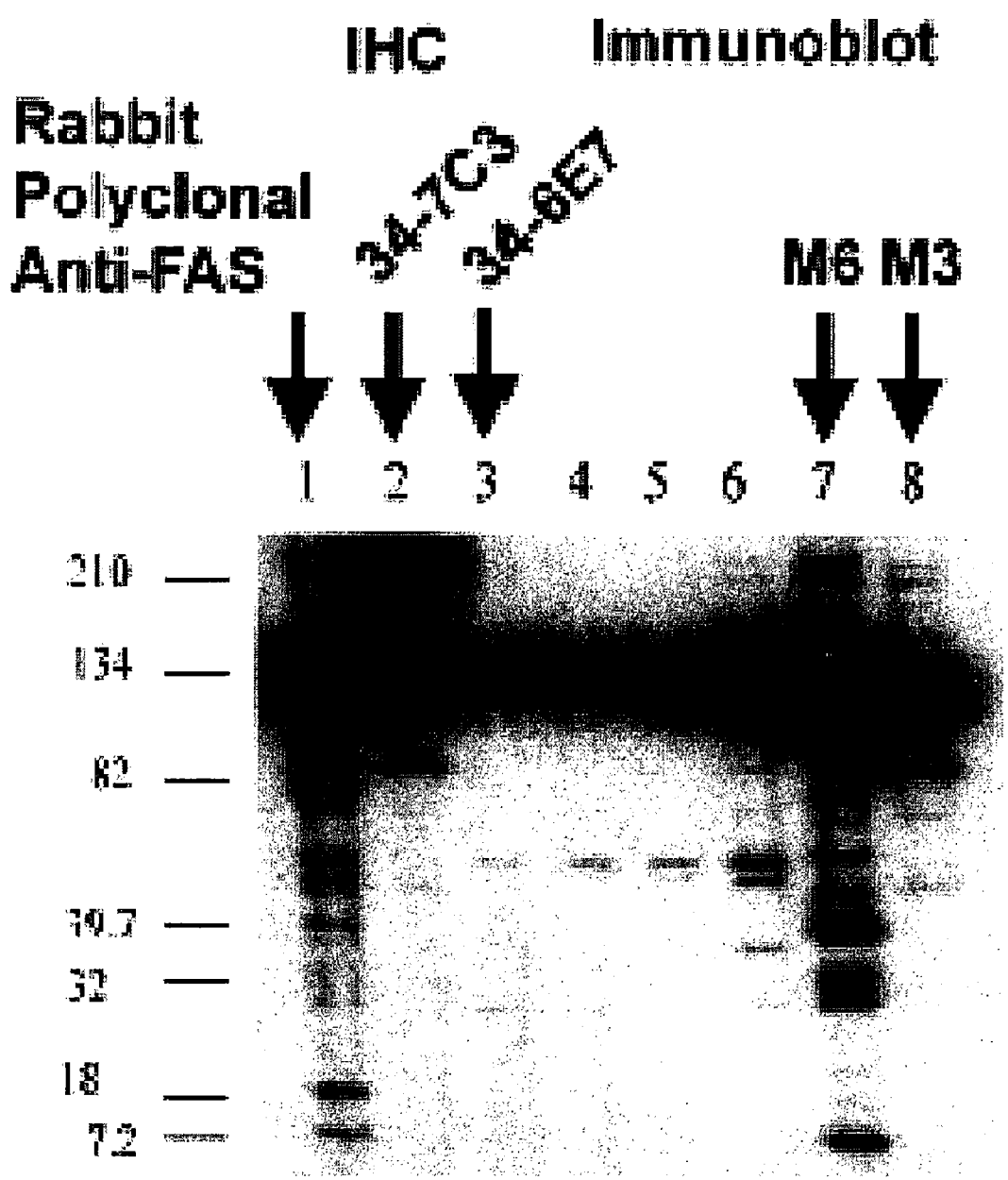

FIG. 2 is an immunoblot of antibodies in FIG. 1 against a tryptic digest of human FAS for epitope mapping.

Figure 3:
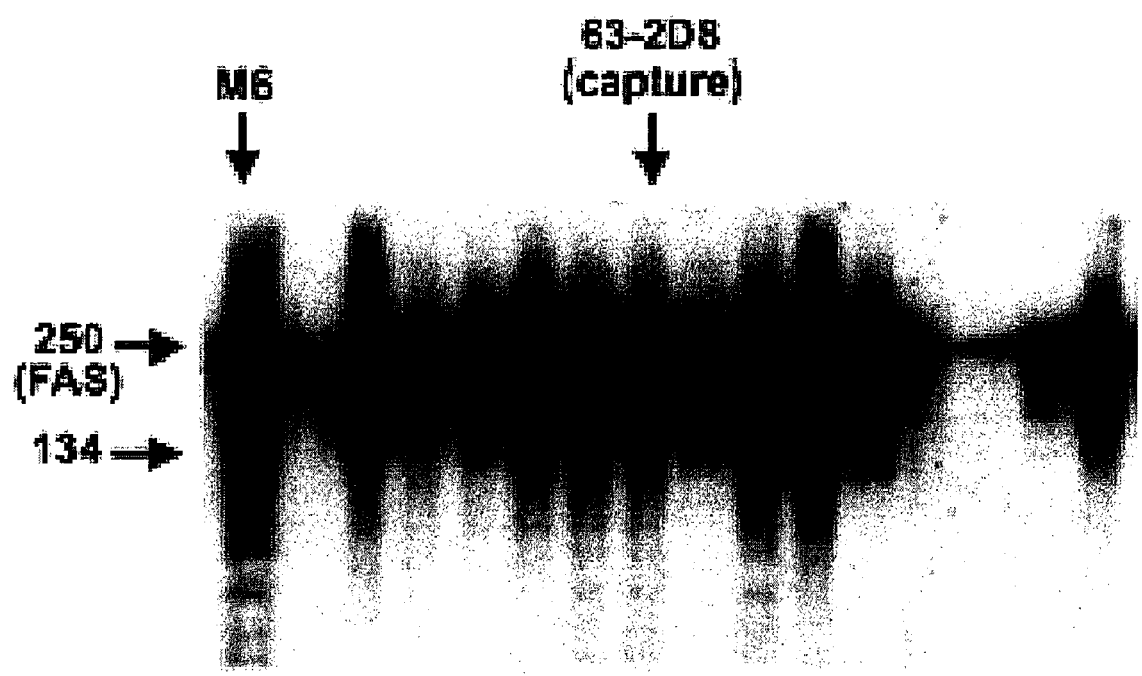

FIG. 3 is an immunoblot of antibodies against a lysate from MCF-7 cells. The results with the M6 antibody (of Wang et al. *J Immunoassay Immunochem*. as cited above) are also shown. The same M6 antibody was used in the remainder of the figures.

Figure 4:
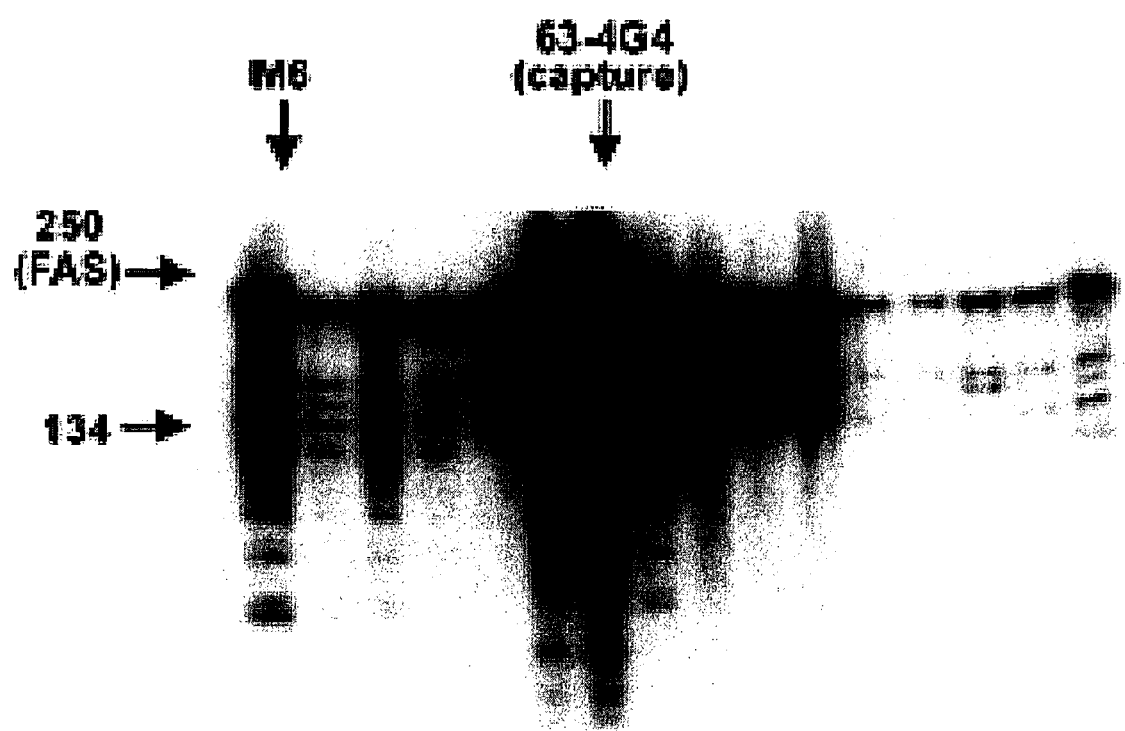

FIG. 4 is an immunoblot of a different group of antibodies against a lysate from MCF-7 cells. The results with the M6 antibody are also shown.

Figure 5:
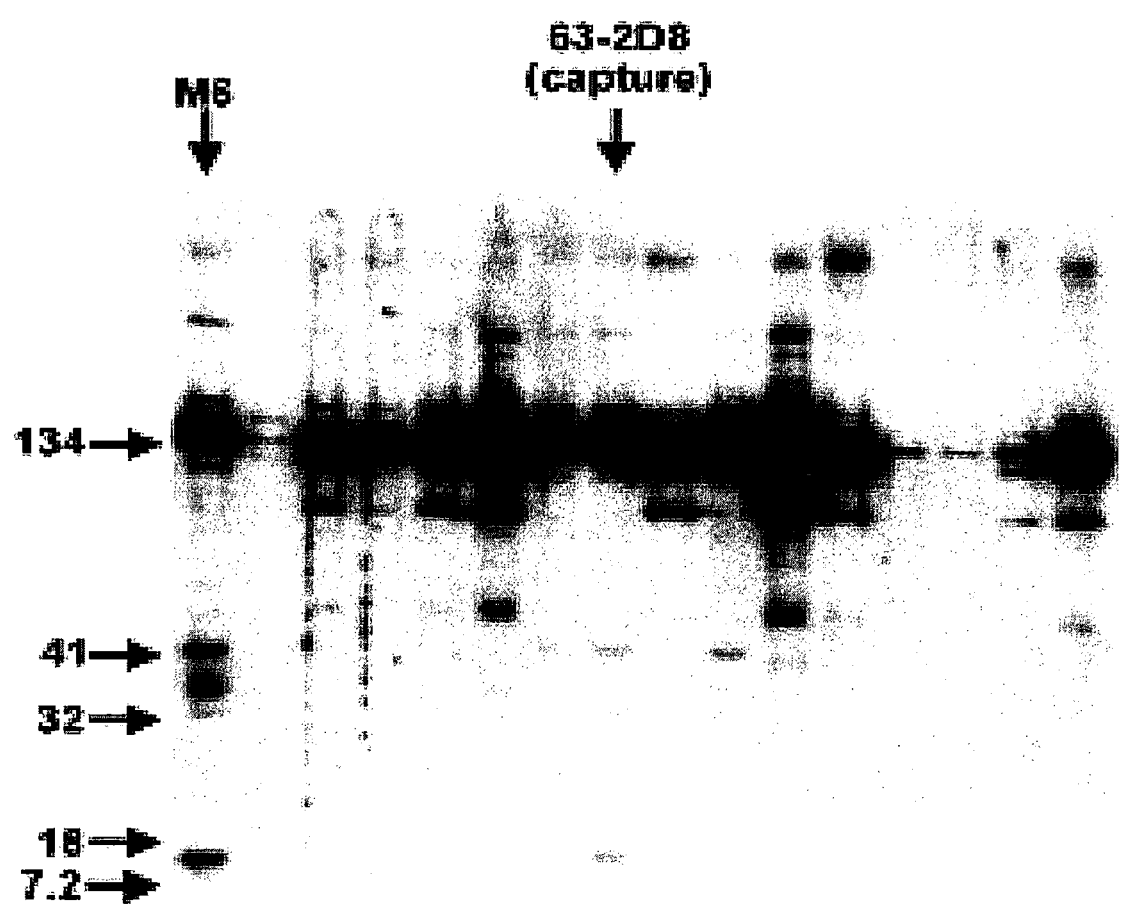

FIG. 5 is an immunoblot of the antibodies of FIG. 3 against a tryptic digest of human FAS purified from ZR-75-1 human breast cancer cells for epitope mapping.

Figure 6:
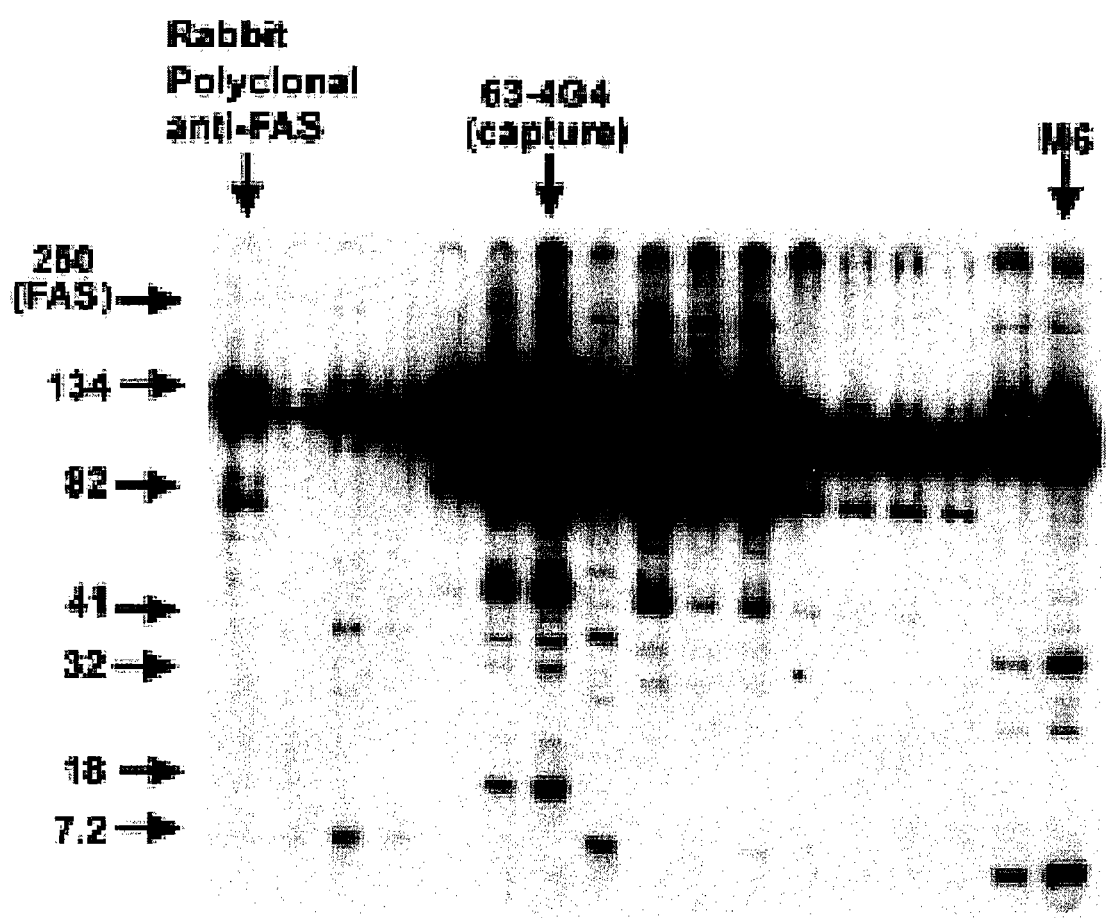

FIG. 6 is an immunoblot of the antibodies of FIG. 4 against a tryptic digest of human FAS purified from ZR-75-1 human breast cancer cells for epitope mapping. The results with a polyclonal antibody and M6 are also shown.

Figure 7:
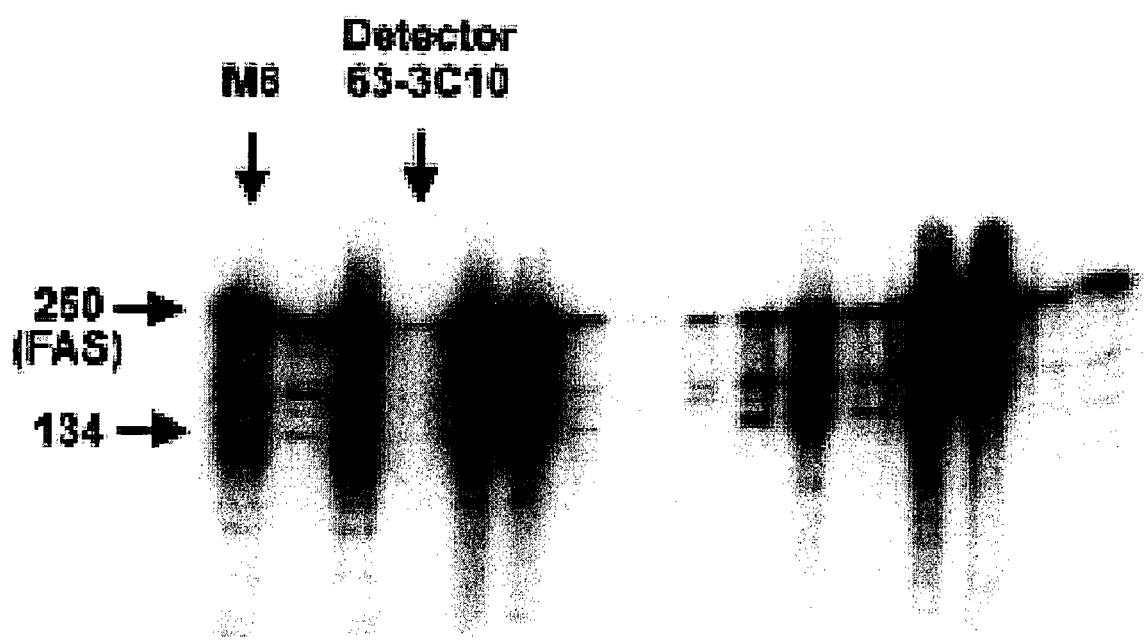

FIG. 7 is an immunoblot of another group of antibodies against a lysate from mCF-7 cells. The results with the M6 antibody are also shown.

Figure 8:
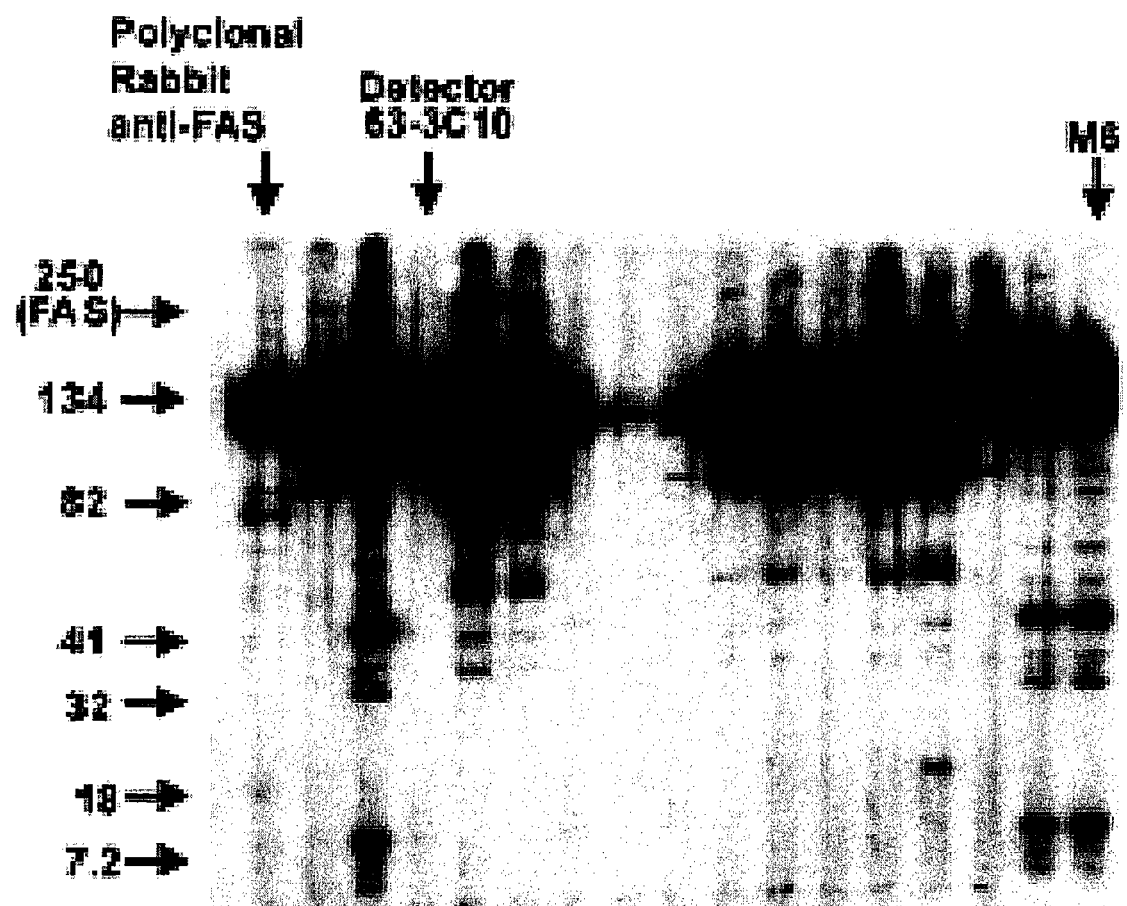

FIG. 8 is an immunoblot of the antibodies of FIG. 7 against a tryptic digest of human FAS purified from ZR-75-1 human breast cancer cells for epitope mapping.

DETAILED DESCRIPTION OF MODES OF PRACTICING THE DISCLOSED INVENTION

The disclosed invention provides antibodies which bind hFAS polypeptides. FAS is a protein expressed in multiple human cell types as well as in cancer cells. The antibodies have specificities of binding that differ from previously known anti-hFAS antibodies. The disclosed invention is based in part on the preparation and analysis of over 120 clones of monoclonal antibodies and the discovery of numerous antibodies that were distinct from previously known monoclonal antibodies against hFAS. Approximately 70 clones have been stored and may be revived. Some clones have been used to produce ascites in animals for antibody production. The disclosed invention is directed to monoclonal antibodies which bind hFAS but are distinct from previously known monoclonal antibodies identified as M3 or M6, or deposited as ATCC accession number 10853.

The ability of an antibody to bind hFAS includes the ability to selectively or specifically bind hFAS under immunologically reactive conditions to one or more determinants of hFAS. The antibodies of the invention may be those which selectively or specifically bind hFAS determinants not present on other molecules, like Hpr as a non-limiting example, that may be found with hFAS in a sample. The term "selectively bind" refers to the preferential association of an antibody, in whole or part, with an epitope present on an hFAS polypeptide and not other polypeptides. It is, of course, recognized that a certain degree of non-specific interaction may occur between an antibody and a non-target molecule. Nevertheless, selective binding, may be distinguished as mediated through specific recognition of hFAS.

Although selectively or specifically binding antibodies bind antigen, they may do so with low affinity. But specific binding results in a much stronger association between the antibody and its cognate antigen than between the antibody and a non-cognate antigen. Specific binding typically results in greater than about 2-fold, greater than about 5-fold, greater than about 10-fold, or greater than about 100-fold increase in the amount of bound antibody (per unit time) to a cognate antigen as compared to a non-cognate antigen. Specific binding to a cognate protein in the presence of non-cognate proteins requires an antibody that is selected for its specificity for a particular antigen. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The binding affinity of antibodies of the disclosed invention may be measured or determined by standard antibody-antigen assays, for example, competitive assays, saturation assays, or standard immunoassays such as ELISA or RIA. Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is <1 μM, preferably <100 nM, and most preferably <0.1 nM. Antibody molecules will typically have a $K_D$ in the lower ranges. $K_D$=[Ab–Ag]/[Ab][Ag] where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible noncovalent associations such as electrostatic attraction, Van der Waals forces and hydrogen bonds. This method of defining binding specificity applies to single heavy and/or light chains, CDRs, fusion proteins or fragments of heavy and/or light chains, that are specific for the cognate antigen if they bind the antigen alone or in combination.

The term "immunologically reactive conditions" refers to conditions which allow an antibody to bind its cognate epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. In some embodiments, the immunologically reactive conditions employed in the methods of the disclosed invention are "physiological conditions" which include reference to conditions (e.g., temperature, osmolarity, and pH) that are typical inside a living mammal or a mammalian cell. While it is recognized that some organs are subject to extreme conditions, the in vivo and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Most antibodies of the disclosed invention retain the ability to bind an hFAS polypeptide of about 250 kD and/or a proteolytic product of hFAS of about 134 kD. In some embodiments, however, the antibodies may bind either of these two hFAS polypeptides with greater or reduced affinity. Alternatively, the antibodies may bind either of these polypeptides with greater or reduced specificity relative to other antigens that may be present with hFAS polypeptides or relative to other hFAS polypeptides.

One means of comparing specificity among different antibodies is to immunoblot the same population of polypeptides or antigens against the different antibodies. The population of polypeptides or antigens may be that of a cell which expresses hFAS or a lysate of such a cell. Non-limiting examples of such cells include a primary cell culture or a cell line which expresses hFAS. Possible cells include breast cancer cells, colorectal cancer cells, and prostate cancer cells as non-limiting examples, while cell lines include MCF-7 and ZR-75-1 as non-limiting examples.

Alternatively, the population of polypeptides or antigens may be that of a partially proteolyzed sample containing hFAS polypeptides. The proteolytic means may be naturally occurring or by use of particular proteolytic agents, such as trypsin, chymotrypsin, Endoproteinase Lys-C or Glu-C, chemical cleavage reagents like cyanogen bromide and BNPS-Skatole, or any other suitable means known in the art. Such populations usually start with partially purified or purified samples of hFAS polypeptides. Non-limiting examples include samples with full length hFAS purified from cells which express hFAS polypeptides without the use of recombinant DNA technology, such as hFAS polypeptides purified from ZR-75-1 cells. Alternatively, the samples may contain hFAS polypeptides expressed by use of recombinant DNA technology.

Antibodies of the invention which specifically bind one or more particular hFAS polypeptides relative to other antigens that may be present with hFAS polypeptides or relative to other hFAS polypeptides may be of particular interest. In some embodiments, the antibodies bind to full length hFAS and/or the 250 kD form with greater affinity or reduced affinity compared to the M3 antibody known in the art.

The disclosed invention also provides antibodies with specificities similar to, but not identical to, the M3 antibody known in the art. Non-limiting examples include hFAS binding antibodies that do not bind an hFAS polypeptide fragment of about 70 kD, and/or that bind an hFAS polypeptide fragment of about 50 kD, in a population of hFAS polypeptides digested with trypsin are provided.

In another embodiment, the disclosed invention provides antibodies with specificities similar to, but not identical to, the M6 antibody known in the art. Non-limiting examples include hFAS binding antibodies that do not bind a polypeptide of about 60 kD, and/or that bind a polypeptide of about 40 kD, in a MCF-7 cell lysate are provided.

Other M6 like antibodies include those which do not bind a polypeptide of a) about 45 kD, about 34 kD, about 16 kD, about 37 kD, about 28 kD, or about 7 kD in a lysate of human ZR-75-1 breast cancer cells digested with trypsin; or b) bind a polypeptide of about 115 kD, about 90 kD, about 50 kD about 85 kD, about 78 kD, about 50 kD, about 40 kD, or about 17 kD in a lysate of human ZR-75-1 breast cancer cells digested with trypsin.

Further M6 like antibodies include those which a) do not bind a polypeptide of about 125 kD, about 32 kD, or about 9 kD in a lysate of human MCF-7 breast cancer cells; or b) binds a polypeptide of about 85 kD, about 50 kD, about 43 kD, or about 24 kD in a lysate of human ZR-75-1 breast cancer cells digested with trypsin.

In further embodiments of the disclosed invention, specific monoclonal antibodies identified as 34-6E7, deposited as hybridoma clone 34-6E7-2G10-15 with the ATCC (10801 University Blvd.. Manassas, VA 20110) on Aug. 17, 2006 and assigned accession number PTA-7814, or 63-2D8, deposited as hybridoma clone 63-2D8-2E2-1D2 with the ATCC on Aug. 17, 2006 and assigned accession number PTA-7817, or 63-4G4, deposited as hybridoma clone 63-4G4-B3-2F3 with the ATCC on Aug. 17, 2006 and assigned accession number PTA-7815, or 63-3C10, deposited as hybridoma clone 63-3C10-2B8 with the ATCC on Aug. 17, 2006 and assigned accession number PTA-7816, are disclosed and specifically contemplated for use in the compositions and methods as described herein. The 34-6E7-2G10-15, 63-2D8-2E2-1D2, 63-4G4-B3-2F3, and 63-3C10-2B8 hybridomas are all mouse hybridoma cell lines originating from mouse spleens. They may be cultured in ImDm with 17.6% fetal bovine serum, 1 mM sodium pyruvate, 2 mM L-glutamine, and 100 units/mL of penicillin-streptomycin. The antibodies produced are all of the $IgG_1$ subtype. Of course antibodies of other subtypes may be prepared by methods known to the skilled person.

The CDRs from these monoclonal antibodies may be isolated in some embodiments of the disclosed invention. Other embodiments include the recombinant application of one or more of the CDRs, or nucleic acids encoding them, to produce fusion proteins or chimeric antibodies for use in the practice of the disclosed invention.

Of course the above discussed hFAS polypeptide fragments may also be used to generate additional antibodies of the invention, including antibodies with the same hFAS reactivity as those detailed herein. As non-limiting examples, the hFAS polypeptide fragment of about 50 kD from a trypsin digestion; the polypeptide of about 40 kD, in a MCF-7 cell lysate; a polypeptide of about 115 kD, about 90 kD, about 50 kD about 85 kD, about 78 kD, about 50 kD, about 40 kD, or about 17 kD in a lysate of human ZR-75-1 breast cancer cells digested with trypsin; and/or a polypeptide of about 85 kD, about 50 kD, about 43 kD, or about 24 kD in a lysate of human ZR-75-1 breast cancer cells digested with trypsin may be isolated by means known to the skilled artisan and used as antigen to generate additional antibodies of the invention. The antibodies may of course be simply screened by use of routine methods known to the skilled person for the hFAS binding reactivities and specificities as described herein.

The anti-hFAS antibodies of the invention may be from any non-human source, including mouse, rat, goat, sheep and rabbit as non-limiting examples. The antibodies may be used as a primary antibody in an immunoassay in combination with a secondary antibody specific for the constant region of the primary antibody. In some embodiments, the primary antibody may be left unlabeled in favor of the secondary antibody being detectably labeled. The antibodies may also be of any class, including IgG, IgM, IgD, IgA, and IgE. They may also be of a subclass of IgG or of IgA.

The antibodies, and fragments thereof, of the invention may also inhibit FAS activity and so act as FAS inhibitors. Such antibodies, and fragments, may be used to both detect the presence of FAS and to inhibit its activity without the need for introduction of an additional FAS inhibitor. Alternatively, an FAS inhibitory antibody or antibody fragment of the invention may be used in combination with another FAS inhibitor, such as in a composition for inhibiting FAS activity or as administered, separately or in combination, to a subject as part of a method to inhibit FAS activity. Without being bound by theory, and offered to improve the understanding of the disclosed invention, an FAS inhibitory antibody or antibody fragment of the invention may act by binding all or part of an FAS binding site and/or regulatory domain. In other embodiments, the administration may be of an antibody or FAS binding portion thereof that is linked or conjugated to another agent such that the antibody (or portion thereof) targets the other agent to the FAS activity. The other agent may be a FAS inhibitor and/or a toxic agent against the cell containing the FAS activity.

In further embodiments, the antibody, or portion thereof, may be delivered to a location of FAS activity via a nucleic acid sequence that encodes the antibody, or portion thereof, separate or as part of a fusion polypeptide. The nucleic acid sequence is thus a coding sequence which may be operably linked to regulatory element(s) such that the element(s) direct the expression of the sequence as an mRNA and/or protein to form an expression construct. Such a construct may be used directly, such as by direct delivery to a desired site followed by uptake by a cell at the site or may be part of a vector construct. Vector constructs of the disclosed invention include those that are capable of self-replication under suitable conditions, such as in permissive cells. Non-limiting examples include viral vectors and plasmid molecules, including those maintained episomally. A plurality of regulatory elements and vectors are known to the skilled artisan and may be readily selected for use in the practice of the disclosed invention.

The antibodies of the invention may be modified or used to derive additional antibodies. Non-limiting examples include hybrid antibodies, altered antibodies, chimeric antibodies, conjugated antibodies, single chain antibodies, and humanized antibodies containing all or part of the hFAS binding functionality of the antibodies of the invention. Other embodiments of the disclosed invention of include portions of the disclosed antibodies which bind hFAS polypeptides, including Fab, Fab', F(ab')$_2$ and Fv fragments.

The disclosed invention includes recombinant anti-hFAS antibody such as a scFv or disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. The antibody may be a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. In a more preferred embodiment, the scFv is recombinantly produced.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., Proc. Nat'l Acad. Sci. USA 8:5879 (1988); Bird, et al., Science 242:4236 (1988); Glockshuber, et al., Biochemistry 29:1362 (1990); U.S. Pat. Nos. 4,946,778, 5,132,405 and Stemmer, et al., Biotechniques 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of a base sequence.

The disclosed invention also provides one or more CDRs from an hFAS binding antibody as provided herein. A CDR may be isolated alone, or in combination with one or both of the other CDRs present on the same antibody light or heavy chain. In some embodiments, isolation is by sequencing and/or isolation of the nucleic acid sequence encoding a CDR (or CDR portion) of an antibody. Such nucleic acid sequences may be recombinantly linked to sequences encoding another polypeptide to form a fusion protein, or used to replace the CDR coding sequences of another antibody to form a chimeric antibody (or fragment thereof), as non-limiting examples. A chimeric antibody containing a CDR of the invention may be used in the same manner as an antibody of the invention.

The antibodies of the invention may be labeled, covalently or non-covalently, as described herein. For use in some immunoassays, an antibody is often labeled to facilitate its detection and thus the detection of an hFAS polypeptide bound to the antibody. In some embodiments, the label may simply be a large particle, including colored glass or plastic (e.g. polystyrene, polypropylene, latex, etc.) beads as non-limiting examples, wherein aggregation of a large number thereof in a localized space is detectable, including to the unaided eye in some exemplary immunoassays.

Where a label or other detectable moiety is to be linked to an antibody of the invention, a number of means known to the skilled person may be used. The procedure for attaching a molecule to an antibody will vary according to the chemical structure of the molecule to be attached. Polypeptides typically contain variety of functional groups which are available for reaction with a suitable functional group on an antibody. Alternatively, the antibody is derivatized to expose or attach additional reactive functional groups. The derivatization may involve attachment of any of a number of linker molecules such as those available from Pierce Chemical Company, Rockford Ill.

Alternatively, the antibodies are used in conjunction with a labeling agent to specifically bind to and label the binding complex formed by the hFAS polypeptide and the antibody. In some embodiments, the labeling agent may itself be one of the moieties comprising the complex, i.e., the anti-hFAS antibody. Alternatively, the labeling agent may be a third moiety, such as another antibody (a secondary antibody that is labeled or immobilized), that specifically binds to the complex. Non-limiting examples of the disclosed invention include the use of a secondary antibody that is species specific to bind the constant region of the anti-hFAS antibody.

In cases of some competitive immunoassays, an unlabeled antibody of the invention is used in combination with a labeled form of another anti-hFAS antibody. The two antibodies are then contacted with hFAS in a sample to compete for binding. In an alternative non-competitive format, the unlabeled anti-hFAS antibody is used in combination with the labeled antibody to form a "sandwich" complex comprising both antibodies and the bound hFAS polypeptide. Detection of this "sandwich" complex is then used to detect the presence of, or determine the amount of, hFAS.

Other proteins which specifically bind immunoglobulin constant regions, such as Protein A or Protein G may also be used as the label agent. These proteins are found as constituents in streptococcal cell walls and exhibit a strong non-immunogenic reactivity with immunoglobulin constant regions from a variety of species (see, generally Kronval, et al., J. Immunol. 111: 1401-1406 (1973); and Akerstrom, et al., J. Immunol, 135:2589-2542 (1985)). Of course the Protein A or Protein G may itself be detectably labeled as described herein, including by attachment or immobilization to a solid phase as provided herein for antibodies of the invention.

The antibodies of the invention may be selected, based upon their different binding specificities, to address the needs of particular situations where detection of hFAS polypeptides is needed. As a non-limiting example, antibodies with greater specificity or affinity for full length hFAS can be selected for use where detection of full length hFAS is desired. Alternatively, antibodies with greater specificity or affinity for a particular hFAS fragment may be used in situations where detection of that fragment is preferred.

The disclosed invention further provides cell lines which express the antibodies of the invention. The cell lines may be hybridoma cell lines, including those deposited as described above.

COMPOSITIONS OF THE DISCLOSED INVENTION

Compositions and preparations comprising the antibodies of the invention include solutions containing the antibodies as well as solid phase materials on which the antibodies have been applied.

In some embodiments, the antibodies are associated with a component or device for the use of the antibodies in an ELISA or RIA. Non-limiting examples include antibodies immobilized on solid surfaces for use in these assays. In another optional embodiment, the antibodies are linked or conjugated to a label that may be electrochemically stimulated and then detected based on light emission. A non-limiting example of such an assay method is electrochemiluminescence (ECL) technology, where an antibody or antibody fragment of the invention is linked to ruthenium chelate so that it can be detected when ruthenium is oxidized/reduced at an electrode surface using known methodologies.

In other embodiments, the antibodies are associated with a device or strip for detection of hFAS polypeptides by use of an immunochromatographic assay, such as one based upon lateral flow of a solution containing hFAS polypeptides as the analyte. These assays may be performed as a "sandwich" or competitive assay. Additional examples of such devices or strips are those designed for home testing or rapid point of care testing. Further examples include those that are designed for the simultaneous analysis of multiple analytes in a single sample.

An unlabeled antibody of the invention may be applied to a "test" or "capture" region of such a device or strip in an immobilized form to capture hFAS polypeptides in the solution as it flows past. In some embodiments, the captured (or immobilized) hFAS polypeptides may be bound to a labeled form of an anti-hFAS antibody of the invention such that the complex of a polypeptide and antibody is captured (or immobilized) in the "test" or "capture" region. The labeled antibody may be associated with, or dried onto, the device in another region of the device or strip such that the antibody contacts said solution before the solution arrives at the "test" or "capture" region. The contact permits the labeled antibody to be dissolved into, and move along with, the solution while also permitting the labeled antibody to form a complex with hFAS polypeptide(s) if present in the solution.

The solution is preferably a biological fluid sample from a subject, such as a human being. The range of biological fluids which may be used in the practice of the disclosed invention includes any fluid in which hFAS may be detectably present. Non-limiting examples include the bodily secretions of a subject, such as saliva, tears, mucous, nasal discharge, and vaginal secretions as well as other bodily fluids such as blood, serum, plasma, semen, seminal fluid, effusions, ascites, cerebrospinal fluid, breast aspirates, fluids of ovarian origin, and urine as well as any fluid component of feces or a fluid extract of feces. Dilutions of such fluids may of course also be used as the sample in the practice of the disclosed invention.

METHODS OF THE DISCLOSED INVENTION

The antibodies of the invention may also be used in methods based upon the detection or measurement of hFAS. While the details of the methods of the disclosed invention may vary with the particular format employed, the method of detecting or measuring hFAS polypeptide(s) in a sample generally comprises the contacting the sample with an antibody which specifically reacts, under immunologically reactive conditions, to the antibody. The antibody may be labeled or unlabeled because antibodies can be detected and/or quantified using any of a number of well recognized immunological binding assays (see, e.g., U.S. Pat. Nos. 4,366,241; 4,376,110; 4,517,288; and 4,837,168).

For a review of general immunoassays that may be practiced with the antibodies of the invention, see also METHODS IN CELL BIOLOGY, VOL. 37, Asai, ed. Academic Press, Inc. New York (1993); BASIC AND CLINICAL IMMUNOLOGY 7TH EDITION, Stites & Terr, eds. (1991). Immunological binding assays (or immunoassays) typically utilize a ligand (hFAS polypeptide(s) as disclosed herein) to specifically bind to and/or immobilize an antibody. In such assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

Other antibody based assay methods provided by the disclosed invention include those based on immuno-diffusion, immunoelectrophoresis, immunohistopathology, immunohistochemistry, and histopathology. The methods may include the use of calorimetric, chemiluminscent, electrochemiluminescent, or fluorescent techniques in combination with an antibody or antibody fragment of the invention. An additional method is the use of a competitive assay as provided by U.S. Pat. No. 5,759,791.

The detection or measurement of hFAS may optionally be performed in the presence of agents to reduce non-specific binding reactions as known to the skilled person. Thus methods including the use of an agent which reduces non-specific binding are provided by the disclosed invention. Non-limiting examples of means to reduce non-specific binding include the use of buffer additives, such as, but not limited to, carrier proteins (like bovine serum albumin), the inclusion of detergent(s), and adjustment of ionic strength.

The detection of the presence of hFAS polypeptides in a sample may be performed as a diagnostic for the presence of a disease, such as cancer. In other embodiments, the disease may be alcoholic hepatitis or steatohepatitis, which is optionally detected via the presence of above normal FAS in liver cells, such as that of a liver biopsy, or in a serum containing fluid as described herein. The detection of alcoholic hepatitis or steatohepatitis may be by use of any FAS binding antibody, including those of the disclosed invention and those previously known to the skilled person.

The detection may be performed as a prognostic indicator of disease outcome, including survival outcome for a subject with a disease associated with increased levels of hFAS expression. The detection may also be used in methods to monitor the course, or recurrence, of a disease in a subject based upon the correlation of the presence, or level, of hFAS to the disease. Non-limiting examples include the likelihood of metastasis of a cancer, the grade of a tumor, and the clinical stage of a disease.

In other embodiments, the detection is used in relation to determining whether to administer a FAS inhibitor to a patient based on the presence or level of hFAS polypeptide(s) in a sample from the patient and the skill or experience of a clinical practitioner or other health care provider. The determination may be directed toward the treatment of disease, which is diagnosed based on the presence or level of hFAS polypeptide(s) in the sample, such that administration of a FAS inhibitor or other agent to treat the disease is palliative. The administration of a FAS inhibitor or other treatment agent may be considered chemotherapy targeted at FAS to treat the disease and/or its symptoms.

In further embodiments, the determination may be used in relation to the prevention of disease, which is indicated as possible based on the presence or level of hFAS polypeptide(s) in the sample and the experience of a skilled practitioner. The determination of a disease state as being possible or likely based upon detection of hFAS is followed by administration of a FAS inhibitor or other agent to prevent the disease from occurring or reducing its severity or extent if it occurs. Thus the disclosed invention includes embodiments in the field of chemoprevention of disease based upon inhibition of fatty acid synthesis.

Additional methods of the disclosed invention include treatment of a subject by administering an antibody, antibody fragment, antibody containing conjugate, or antibody containing fusion polypeptide as described herein to inhibit FAS activity or target a site wherein FAS is expressed or present. Non-limiting examples include direct administration of an antibody of the invention to a subject, such as injection into a cell containing portion of a subject's body to allow uptake of the antibody. Alternatively, a nucleic acid molecule or construct encoding an antibody of the invention may be administered, such as by direct injection into a cell containing portion of a subject's body, to allow cellular uptake of the nucleic acid followed by expression of the antibody. The subject may be a human being, and the disclosed invention provides for analogous methods comprising administration of an antibody fragment, antibody containing conjugate, or antibody containing fusion polypeptide as described herein.

Uses in Medical Care

The disclosed invention also provides for the detection of, or measurement of, hFAS polypeptide(s) as one component in the providing of medical care to a patient. Non-limiting examples include the providing of diagnostic services in conjunction with providing treatment as medical care. Thus the disclosed invention includes a method in the medical care of a patient, the method comprising measuring the presence or expression of hFAS in a sample obtained from the patient. A method in the medical care of a patient may comprise any method as disclosed herein. The method optionally includes interpretation of the results from the detection or measurement of hFAS. The detection or measurement may be for use in relation to any aspect or embodiment of the invention as described herein.

As one non-limiting example, the detection or measurement may be preceded by a determination of a need for assessing hFAS, such as a determination by a medical doctor, nurse or other health care provider, or those working under their instruction. The determination may also have been made by personnel of a health insurance or maintenance organization in approving the performance of the detection or measurement as a basis to request reimbursement or payment for the performance.

In another non-limiting embodiment, the disclosed invention provides a method of ordering, or receiving an order for, the performance of a method in the medical care of a patient or other method as described herein. The ordering may be made by a medical doctor, a nurse, or other health care provider, or those working under their instruction, while the receiving of an order, directly or indirectly, may be by any personnel who performs the methods.

The disclosed invention also provides methods in the processing of payment or reimbursement for a detection or measurement of hFAS as described herein. A method in the processing of reimbursement or payment may comprise making an indication that 1) payment is pending or yet to be received or past due, 2) payment has been received, 3) payment is insufficient or inadequate, or 4) payment will be made by another payer, on paper or electronically, such as in a database or other computer readable medium after performance of a hFAS detection or measurement method of the disclosed invention. The database may be in any form, including electronic forms such as a computer implemented database as a non-limiting example. The indication made may be in the form of, or include, a code on paper or in electronic (or computer readable) form. In some embodiments of the disclosed invention, the code may include 88342 for immunohistochemistry interpretation. Where "another payer" is implicated, request for payment may be to a person or entity beyond the original payer to whom a previous invoice or statement for payment or was sent or communicated.

Alternatively, the method may comprise receiving payment for the technical performance of a method of detecting or measuring hFAS in the medical care of a patient or for the interpretation of the results there from. Of course the disclosed invention also includes embodiments wherein another person or party receives payment or is instructed to receive payment. The receipt may be from any entity, including an insurance company, health maintenance organization, governmental (health) agency, a patient, or family member of the patient as non-limiting examples. The payment may be in whole or in part. In the case of a patient, the payment may be in the form of a partial payment known as a co-pay.

In yet another embodiment, the method may comprise forwarding, or having forwarded, an invoice or other request for payment to an insurance company, health maintenance organization, governmental health agency, or to a patient for the performance of the a method comprising detecting or measuring hFAS in the medical care of a patient. The request may be made by mail, electronically, telephonically, in person, or by facsimile.

In a further embodiment, a method may comprise receiving indication of approval for payment, or denial of payment, for performance of a method of detecting or measuring hFAS in the medical care of a patient. Such an indication may come from any person or party to whom a request for payment was made. Non-limiting examples include an insurance company, health maintenance organization, or a governmental (health) agency, like Medicare or Medicaid as non-limiting examples. The indication may be by mail, electronically, telephonically, in person, or by facsimile.

An additional embodiment is a method comprising sending a request for reimbursement for performance of a method of detecting or measuring hFAS in the medical care of a patient. Such a request may be made by mail, electronically, telephonically, in person, or by facsimile. The request may have been made to an insurance company, health maintenance organization, federal (health) agency, or the patient for whom the method was performed.

A further method comprises indicating the need for reimbursement or payment on a form or into a database for performance of a method of detecting or measuring hFAS in the medical care of a patient. Alternatively, the method may simply comprise indicating the performance of the method. The database may be in any form, with electronic forms such as a computer implemented database included as a non-limiting example. The indicating may be in the form of a code or other indication on paper or in the database.

In the above methods in the medical care of a patient, the method may comprise reporting the results of the method, optionally to a health care facility, a health care provider, a doctor, a nurse, or personnel working therefore. The reporting may also be communicated directly or indirectly to the patient. The reporting may have been by mail, electronically, telephonically, in person, or by facsimile.

Pharmaceutical Compositions and Administration

Pharmaceutical compositions comprising an antibody, antibody fragment, antibody containing conjugate, or antibody containing fusion polypeptide of the invention are also provided. Such pharmaceutical preparations and formulations may be used in the methods described herein. Non-limiting examples include diagnostic methods of the disclosed invention for detection of FAS and therapeutic methods of the disclosed invention, where a therapeutic FAS inhibitor is administered following detection of FAS as described herein. Alternative non-limiting embodiments include the administration of a toxin conjugated antibody or antibody fragment, or administration of an antibody or antibody fragment that directly inhibits FAS activity. Compositions comprising an antibody or antibody fragment of the invention in combination with another FAS inhibitor are also provided. In many embodiments, compositions and formulations of the disclosed invention are for use with human subjects in vivo or ex vivo. Compositions and formulations may of course include a pharmaceutically acceptable diluent, excipient, salt and/or (protein) stabilizer.

In both therapeutic and diagnostic applications, an antibody or antibody fragment of the invention may be formulated for different modes of administration, including systemic or localized administration. General techniques and formulations known to the skilled person are found in Remington: The Science and Practice of Pharmacy (20th ed.) Lippincott, Williams & Wilkins (2000).

An antibody or antibody fragment of the invention may be used over a range of amounts. The exact amount will depend upon the route of administration, the form in which an antibody or fragment thereof is administered, the subject to be treated (depending upon factors such as the body weight of the subject), and the preference and experience of the skilled person, such as a physician.

Pharmaceutically acceptable diluents and excipients are physiological tolerable and compatible. Non-limiting examples include water, saline, dextrose, glycerol, or the like, and combinations thereof. Additionally, and if desired, a composition or formulation may contain an auxiliary substance such as a wetting or emulsifying agent, or a pH buffering agent.

Pharmaceutically acceptable salts are known to the skilled person. Non-limiting examples include, but are not limited to, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other acceptable salts and agents are found, for example, in Remington as cited above.

Compositions and formulations may be prepared for parenteral delivery, including intramuscular, subcutaneous, intramedullary injections, as well as intrathecal, direct intraventricular, intravenous, intraperitoneal, intranasal, or intraocular injections. Preparations for transdermal administration are also provided. One non-limiting example is seen in the topical application to melanoma on or near the surface of a subject.

Direct delivery of a composition is provided by the disclosed invention. Non-limiting examples include direct injection into the site of a tumor, such as into the tumor itself, or into a particular tissue, such as the liver. As a further non-limiting example, delivery may be to a site of liver tissue after resection. Thus localized delivery may be used in the practice of the disclosed invention.

An antibody or antibody fragment of the invention may be formulated in aqueous solutions, for example, in physiologically compatible buffers such as Hank's solution, Ringer's solution, or physiological saline buffer. In some embodiments, inclusion of a penetrant appropriate to the barrier to be permeated are included. Such penetrants are known to the skilled person. A pharmaceutically acceptable carrier may also be used in a composition or formulation for the practice of the disclosed invention as dosages for systemic administration. A composition or formulation may also be in the form of a suspension or solid form suitable for solution in, or suspension in, a liquid prior to injection.

Pharmaceutical compositions for use in the disclosed invention include those wherein an antibody or fragment thereof are present in an effective amount to achieve its intended purpose.

Compositions comprising a nucleic acid molecule encoding an antibody, antibody fragment, or antibody containing fusion polypeptide of the invention are also provided. Such compositions may be formulated depending on the nature of the nucleic acid, such as, but not limited to, whether it is the molecule per se or the molecule in the form of a packaged viral vector, that is to be administered.

The compositions may be formulated for parenteral delivery, including intramuscular, subcutaneous, intramedullary injections, as well as intrathecal, direct intraventricular, intravenous, intraperitoneal, intranasal, or intraocular injections. Preparations for transdermal administration, such as to melanoma on the surface of a patient, are also provided.

Localized or direct delivery of a nucleic acid of the disclosed invention is also provided. Non-limiting examples include direct injection into the site of a tumor, such as into the tumor itself, or into a particular tissue, such as the liver such that the nucleic acid will be taken up by cells at or near the site of injection. After uptake, the nucleic acid, which is capable of expressing the encoded antibody or antibody related polypeptide, will be expressed to produce antibody or antibody related polypeptide in the cells. As a further non-limiting example, delivery of a nucleic acid capable of expressing an antibody or antibody related polypeptide in a liver cell may be to a site of liver tissue after resection to result in the expression of hFAS binding activity in that location.

Kits of the Disclosed Invention

The disclosed invention provides kits for the detection of hFAS or an immunoreactive fragment thereof, (i.e., collectively, a "hFAS protein") in a biological sample as described herein. Biological samples also include sections of tissues, such as fresh, frozen or fixed sections taken for histological purposes. A kit will typically comprise an anti-hFAS antibody of the disclosed invention or a preparation of antibodies that is immunoreactive with epitopes present on an hFAS polypeptide. In some embodiments, the anti-hFAS antibody will be an antibody fragment.

A kit of the disclosed invention may also include instructional materials disclosing or describing the use of the kit or an antibody of the disclosed invention in a method of the disclosed invention as provided herein. A kit may also include additional components to facilitate the particular application for which the kit is designed. Thus, for example, a kit may additionally contain means of detecting the label (e.g. enzyme substrates for enzymatic labels, filter sets to detect fluorescent labels, appropriate secondary labels such as a sheep anti-mouse-HRP, or the like). A kit may additionally include buffers and other reagents recognized for use in a method of the disclosed invention. Non-limiting examples include agents to reduce non-specific binding, such as a carrier protein or a detergent.

In some embodiments of the disclosed invention, the kit is a diagnostic kit comprising an immunoassay as described herein. Although the details of the immunoassays of the disclosed invention may vary with the particular format employed, the method of detecting hFAS in a sample generally comprises the contacting of the sample with an antibody which specifically reacts, under immunologically reactive conditions, to hFAS. The antibody is allowed to bind to hFAS under immunologically reactive conditions, and the presence of the bound antibody is detected directly or indirectly.

Having now generally described the invention, the same will be more readily understood through reference to the following examples which are provided by way of illustration, and are not intended to be limiting of the disclosed invention, unless specified.

EXAMPLES

Example 1

Antibody Production

General methods of producing polyclonal antibodies are known to the skilled person in the field. Additionally, methods for the preparation of monoclonal antibodies as well as derivatives and fragments thereof are known. Typically, both include the use of hFAS protein or polypeptides thereof to immunize an antibody producing animal. The hFAS protein may be a purified material that has been obtained from a suitable source, such as, but not limited to, human cells that produce hFAS protein.

As a non-limiting example, a procedure adapted from Linn TC (1981) Arch. Biochem. Biophys. 209, 613-619 may be used. Briefly, ZR-75-1 cells are grown to approximately 80-90% confluence, rinsed with HBSS and lysed on ice. The lysed cells are scraped off and homogenized on ice followed by centrifugation at 4° C. The supernatant is removed and resuspended in lysis buffer (20 mM Tris-HCl, ph 7.5, 1 mM EDTA, 0.1 mM PMSF, 0.1% Igepal CA-630) with 7.5% PEG (average MW 8000).

The resultant solution is rocked at 4° C. for 60 minutes, centrifuged at 4° C. followed by removal of supernatant to a new bottle. PEG 8000 in lysis buffer is added until final concentration of PEG is 15% followed by repeat of the rocking and centrifugation steps. Remove supernatant and resuspend pellet in 20 mM $K_2HPO_4$, pH 7.4, and rock solution at 4° C. overnight followed by filtration through a 0.45 μm filter. Load filtered solution onto a Mono Q column and elute with 20 mM $K_2HPO_4$, pH 7.4, in a continuous gradient up to 1M KCl. Analyze fractions by SDS-polyacrylamide gel electrophoresis for FAS. Identify and pool fractions containing FAS of approximate MW 270 kD.

In the preparation of antibodies of the invention, however, it may be preferred to not use an immunogen or methods as provided in Example 16 of U.S. Pat. No. 5,759,791 in order to reduce the likelihood of producing a monoclonal antibody as described therein. As a non-limiting example, intrasplenic immunization as known to the skilled person may be used (see for example *Journal of Tissue Culture Methods*, 12:3, 1989). The M3, M6, and anti-Hpr antibodies were not prepared by use of intrasplenic immunization.

Example 2

ELISA Antigen Capture to Detect FAS Protein

Rows of an ELISA plate were coated with 100 μl per well of Positive Capture Antibody at a 2.5 μg/ml of each Mab in combination: 63-2D8 and 63-4G4 (5 μg/ml total antibody) in PBS coating buffer (Sigma Cat# P-3813, or equivalent). Other rows were coated with 100 μl per well of Negative Capture Antibody at a 2.5 μg/ml of each Mab in combination: two Mabs directed to antigen other than FAS (5 μg/ml total antibody) in PBS coating buffer. The coated plates could be stored at 4° C., overnight. The plates were washed 4 times with PBS wash buffer (Sigma Cat# P-3813, or equivalent with Tween-20 and thimerosal).

Plates were blocked with 150 μl per well of ELISA Dilution/Blocking Buffer (Sigma Cat# P-3813, or equivalent with Hepes, Triton-X, BSA, normal goat IgG, normal rabbit IgG, and mouse MAb) and incubated 1 hour at 37° C. The plates were washed 4 times with PBS wash buffer. hFAS protein (positive antigen), negative antigen, and unknowns were added to the plate.

A titration of hFAS protein was performed by serially diluting the protein, from 313 ng/ml to 1.2 ng/ml in ELISA Dilution/Blocking Buffer, on the ELISA plate in both positive and negative coated wells. Each set of wells contains 100 μl of each antigen dilution once titration is performed. Add ELISA Dilution/Blocking Buffer to at least 3 wells of negative and positive coated wells, as negative antigen controls. Unknown samples were diluted 1:2 in Dilution/Blocking Buffer, in 100 μl volume, are added to duplicate wells of both positive and negative capture coated wells.

Plates were incubated for 1 hour at 37° C. and then washed 4 times with PBS wash buffer. 100 μl of biotinylated detector antibody Mab: 63-3C10 was added at a concentration of 0.313 μg/ml in ELISA Dilution/Blocking buffer to each well. Plates were incubated for 1 hour at 37° C. followed by washing 4 times with PBS wash buffer.

100 μl Conjugate (HRP-labeled streptavidin), diluted to 0.05 μg/ml, was added to each well. The plates were incubated for 1 hour at 37° C. and washed 4 times with PBS wash buffer. Substrate (ABTS 2-component) was prepared and 100 μl of combined substrate was added to each well followed by incubation for 30 minutes at 37° C.

Optical density (OD) between 405 and 410 nm was measured. OD values are compared between the negative antigen controls and the FAS standard curve. Sensitivity or lowest point of detection (LPD) is determined by choosing the concentration of FAS at the OD value greater than the mean value of the negative antigen controls. The LPD should normally be approximately 0.100 greater than the mean of the negative control. It should be noted, however, that the above definition of LPD is arbitrary and that other LPD's may be used in the practice of the disclosed invention. The OD values in the negative capture wells should be below 0.300 OD for all samples and controls.

The ELISA plates could be read by the unassisted eye. A color change in the well with greater intensity than the no antigen (negative) controls are considered positive.

All references cited herein, including patents, patent applications, and publications, are hereby incorporated by reference in their entireties, whether previously specifically incorporated or not.

Having now fully described the invention, it will be appreciated by those skilled in the art that the same can be performed within a wide range of equivalent parameters, concentrations, and conditions without departing from the spirit and scope of the invention and without undue experimentation.

While the invention has been described in connection with specific embodiments thereof, it will be understood that it is capable of further modifications. This application is intended to cover any variations, uses, or adaptations of the invention following, in general, the principles of the invention and including such departures from the disclosure as come within known or customary practice within the art to which the invention pertains and as may be applied to the essential features hereinbefore set forth.

What is claimed is:

1. A monoclonal antibody, or antigen binding fragment thereof, which specifically binds human fatty acid synthase (hFAS), wherein the antibody is 34-6E7, deposited as hybridoma clone 34-6E7-2G10-15 with the ATCC and assigned accession number PTA-7814, or 63-2D8, deposited as hybridoma clone 63-2D8-2E2-1D2 with the ATCC and assigned accession number PTA-7817, or 63-4G4, deposited as hybridoma clone 63-4G4-B3-2F3 with the ATCC and assigned accession number PTA-7815, or 63-3C10, deposited as hybridoma clone 63-3C10-2B8 with the ATCC and assigned accession number PTA-7816.

2. A cell line which expresses the antibody, or fragment thereof, of claim 1.

3. A composition comprising a complex of the antibody, or fragment thereof, according to claim 1 and an hFAS polypeptide, wherein said antibody, or fragment thereof, is optionally labeled.

4. A method of detecting a FAS polypeptide by immunohistochemistry, said method comprising detecting said polypeptide in a sample with the antibody, or fragment thereof, according to claim 1.

5. A device or kit comprising the antibody, or fragment thereof, according to claim 1, said device or kit optionally comprising a label to detect said antibody, or fragment thereof, or a complex comprising said antibody.

6. The device or kit of claim 5, wherein said device is a lateral flow device which detects hFAS in a sample by use of a sandwich assay or a competition assay.

7. A method of detecting an hFAS polypeptide, said method comprising
forming a complex comprising the antibody, or fragment thereof, of claim 1 and an hFAS polypeptide; and
detecting said complex, optionally with an enzyme linked immunosorbent assay (ELISA) or radioimmune assay (RIA).

8. The method of claim 7 wherein said hFAS polypeptide is in a sample from a subject and detection of said complex indicates the a presence of cancer in said subject.

9. A method of monitoring a disease in a subject, said method comprising
determining an amount of an hFAS polypeptide in a sample from said subject based on formation of a complex comprising the antibody, or fragment thereof, of claim 1 and said hFAS polypeptide;
wherein said determining is optionally with an enzyme linked immunosorbent assay (ELISA) or radioimmune assay (RIA) and
wherein said amount of hFAS indicates a course, or recurrence, of said disease.

10. The method of claim 9 wherein said disease is cancer.

11. A method of determining whether to administer a FAS inhibitor to a subject, said method comprising
determining an amount of an hFAS polypeptide in a sample from said subject based on formation of a complex comprising the antibody, or fragment thereof, of claim 1 and said hFAS polypeptide; and
determining whether to administer a FAS inhibitor based on said amount of hFAS detected
wherein said determining is optionally with an enzyme linked immunosorbent assay (ELISA) or radioimmune assay (RIA).

12. A method of providing chemoprotection to a subject with pre-malignant cells, said method comprising
determining an amount of an hFAS polypeptide in a sample from said subject based on formation of a complex comprising the antibody, or fragment thereof, of claim 1 and said hFAS polypeptide; and
administering an FAS inhibitor to said subject based upon said amount of hFAS detected to provide chemoprotection to said subject,
wherein said determining is optionally with an enzyme linked immunosorbent assay (ELISA) or radioimmune assay (RIA).

* * * * *